(12) United States Patent
Srinivasan

(10) Patent No.: US 8,147,396 B2
(45) Date of Patent: Apr. 3, 2012

(54) NEONATE IMAGING SUB-SYSTEM

(75) Inventor: Ravi Srinivasan, Beachwood, OH (US)

(73) Assignee: Advanced Imaging Research, Inc., Cleveland, OH (US)

( * ) Notice: Subject to any disclaimer, the term of this patent is extended or adjusted under 35 U.S.C. 154(b) by 1680 days.

(21) Appl. No.: 10/997,338

(22) Filed: Nov. 24, 2004

(65) Prior Publication Data

US 2005/0113668 A1 May 26, 2005

Related U.S. Application Data

(60) Provisional application No. 60/525,273, filed on Nov. 26, 2003, provisional application No. 60/722,760, filed on Nov. 26, 2003, provisional application No. 60/723,325, filed on Nov. 26, 2003.

(51) Int. Cl.
*A61G 11/00* (2006.01)

(52) U.S. Cl. .............. 600/22; 600/411; 324/318; 5/601; 5/603

(58) Field of Classification Search .................. 600/407, 600/411, 22, 415, 421, 422; D24/163; 378/4, 378/17, 20, 21, 69, 195, 198, 209; 324/318; 5/601, 603
See application file for complete search history.

(56) References Cited

U.S. PATENT DOCUMENTS

| | | | | |
|---|---|---|---|---|
| 1,871,005 A | * | 8/1932 | Mutscheller et al. | 378/179 |
| 3,626,186 A | * | 12/1971 | Allard et al. | 378/174 |
| 3,821,947 A | * | 7/1974 | Schossow | 600/22 |
| 3,858,570 A | * | 1/1975 | Beld et al. | 600/22 |
| 5,370,118 A | * | 12/1994 | Vij et al. | 600/422 |
| 5,619,996 A | * | 4/1997 | Beresten | 600/422 |
| 5,800,335 A | | 9/1998 | Koch et al. | |
| 6,029,082 A | * | 2/2000 | Srinivasan et al. | 600/422 |
| 6,322,250 B1 | * | 11/2001 | Pratt | 378/208 |
| 6,356,081 B1 | * | 3/2002 | Misic | 324/318 |
| 6,409,654 B1 | * | 6/2002 | McClain | 600/22 |
| 6,424,854 B2 | * | 7/2002 | Hayashi et al. | 600/415 |
| 6,459,923 B1 | * | 10/2002 | Plewes et al. | 600/411 |
| 6,577,888 B1 | * | 6/2003 | Chan et al. | 600/422 |
| 6,611,702 B2 | | 8/2003 | Rohling et al. | |
| 6,722,783 B2 | * | 4/2004 | Jackson, Sr. | 378/178 |
| 6,776,527 B1 | * | 8/2004 | Tybinkowski et al. | 378/209 |
| 6,867,593 B2 | * | 3/2005 | Menon et al. | 324/318 |
| 6,893,156 B2 | * | 5/2005 | Sharpensteen et al. | 378/177 |
| 6,926,441 B2 | * | 8/2005 | Stout, Jr. | 378/177 |
| 6,973,689 B2 | * | 12/2005 | Lenting et al. | 5/601 |
| 6,980,002 B1 | * | 12/2005 | Petropoulos et al. | 324/318 |
| 6,992,486 B2 | * | 1/2006 | Srinivasan | 324/318 |

(Continued)

FOREIGN PATENT DOCUMENTS

WO 98/48756 A1 11/1998

(Continued)

*Primary Examiner* — Brian Casler
*Assistant Examiner* — Amanda Lauritzen
(74) *Attorney, Agent, or Firm* — Renner, Otto, Boisselle & Sklar, LLP

(57) ABSTRACT

A radiographic imaging sub-system for treating neonates is disclosed. The subsystem includes a radiographic compatible incubator for providing a controlled environment for a neonate, a radiographic compatible RF coil selectively coupled to the incubator for providing radiographic imaging of the neonate, and a radiographic compatible trolley for transporting the incubator and the RF coil. Additionally, the sub-system can include a radiographic MR compatible vital signs monitor, a radiographic compatible infusion pump, a radiographic compatible injector, a radiographic compatible ventilator, a radiographic compatible blender, radiographic compatible intravenous pole, tanks, pressure reducers/gauges and flow pipes.

22 Claims, 7 Drawing Sheets

U.S. PATENT DOCUMENTS

| | | | |
|---|---|---|---|
| 7,016,467 B2 * | 3/2006 | Brooks | 378/102 |
| 7,215,120 B2 * | 5/2007 | Vaughan | 324/318 |
| 2002/0082468 A1 * | 6/2002 | Goldberg et al. | 600/22 |
| 2002/0173717 A1 * | 11/2002 | Rohling et al. | 600/415 |
| 2003/0153805 A1 * | 8/2003 | Gryn et al. | 600/22 |
| 2004/0020675 A1 * | 2/2004 | Bally et al. | 174/50 |
| 2004/0116799 A1 * | 6/2004 | Srinivasan | 600/410 |
| 2005/0107686 A1 * | 5/2005 | Chan et al. | 600/422 |
| 2005/0215844 A1 * | 9/2005 | Ten Eyck et al. | 600/22 |
| 2007/0016003 A1 * | 1/2007 | Piron et al. | 600/415 |
| 2008/0007250 A1 * | 1/2008 | Wiggins | 324/200 |
| 2008/0024133 A1 * | 1/2008 | Vaughan et al. | 324/318 |

FOREIGN PATENT DOCUMENTS

WO 02/83053 A1 4/2002

* cited by examiner

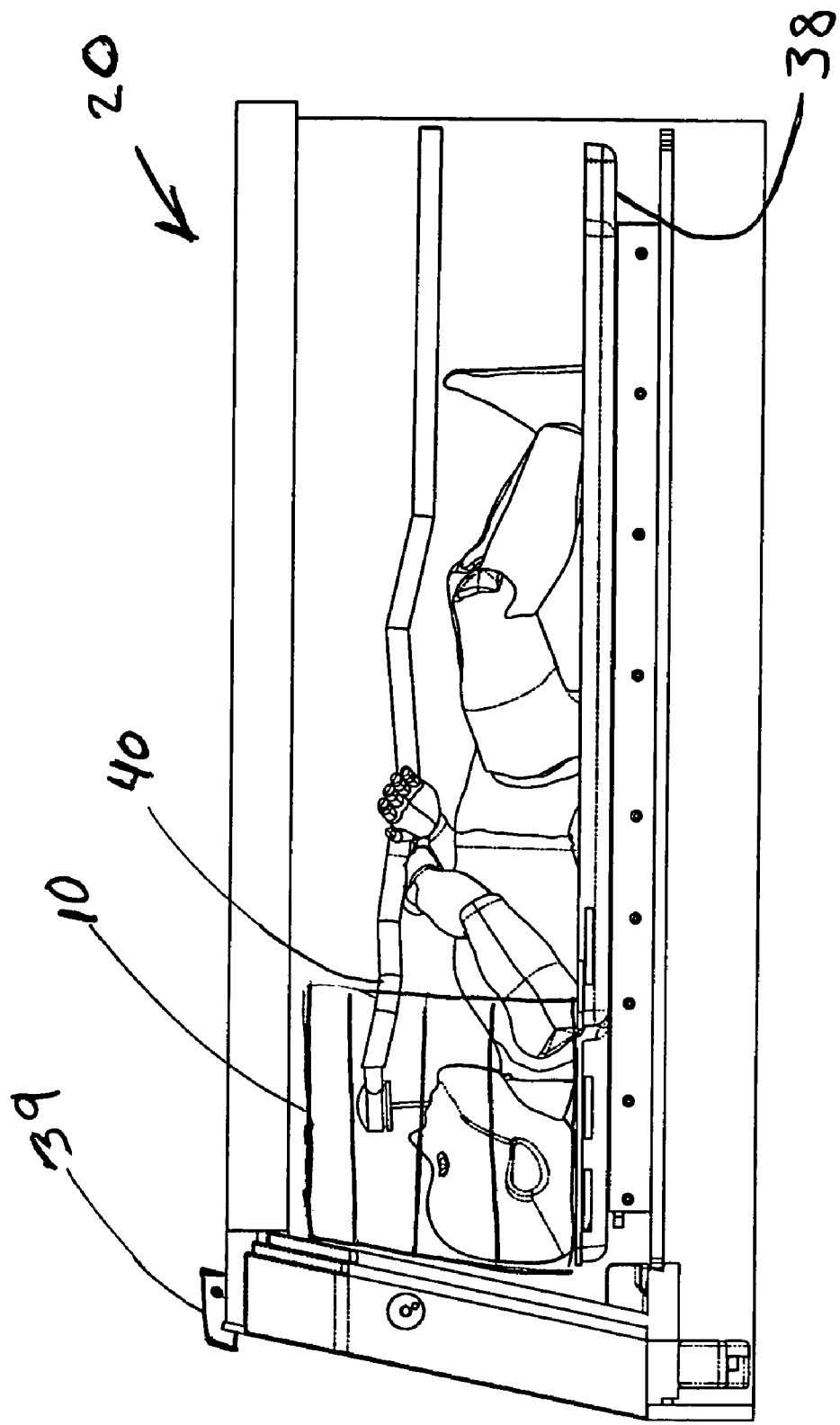

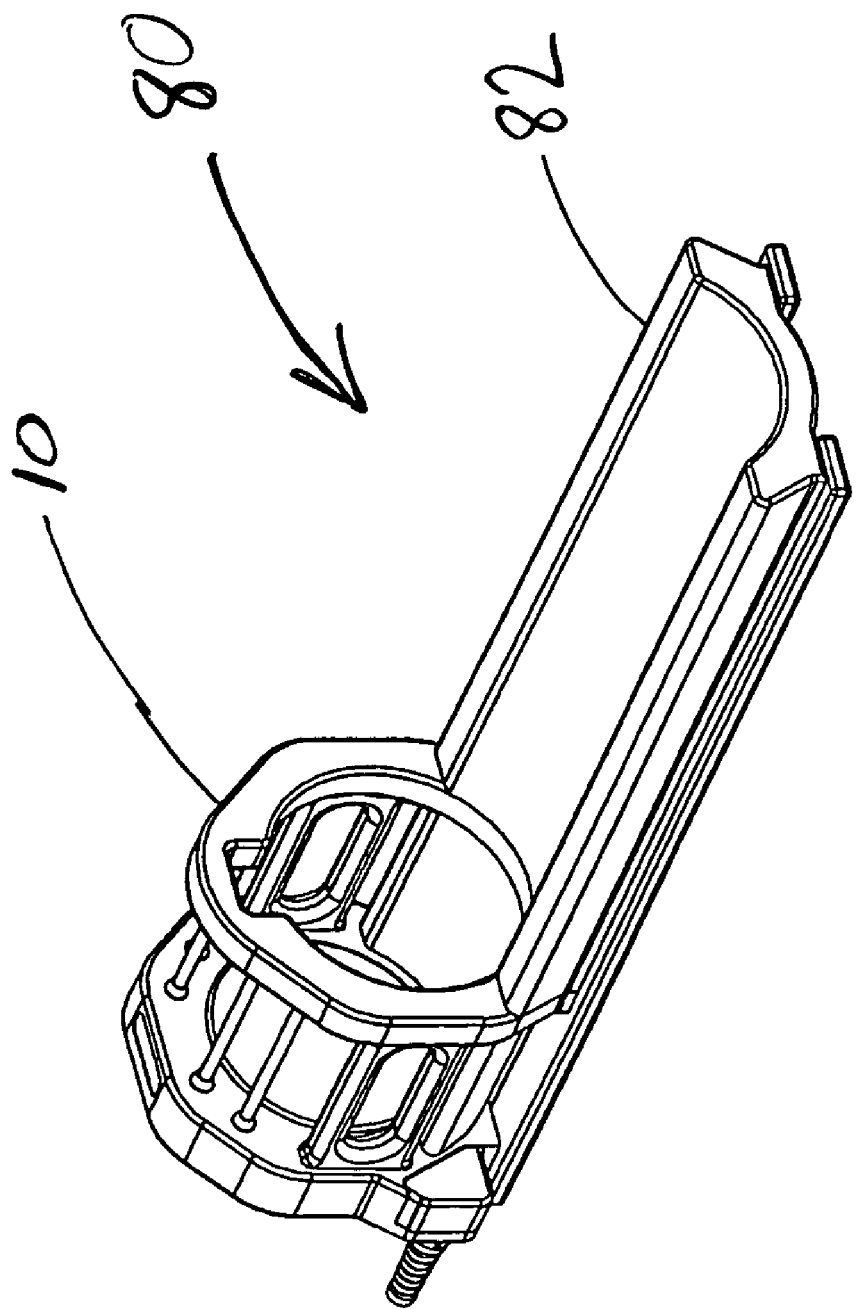

NEONATE IMAGING SUB-SYSTEM

CROSS REFERENCE TO RELATED APPLICATIONS

This Application claims priority from U.S. Provisional Application Ser. Nos. 60/525,273, 60/722,760 and 60/723,325 all filed on Nov. 26, 2003, and incorporated herein by reference.

TECHNICAL FIELD

The present invention relates to a self-contained neonate imaging sub-system for transporting sick newborns within a hospital (intra-hospital) and to and from a hospital. More specifically, the invention relates to a self contained neonate imaging sub-system that is safe for patient transport and for use with diagnostic radiology techniques (such as, magnetic resonance (MR), Computer Tomography (CT), X-Ray techniques etc.) and to perform clinical interventions (such as radiation therapy for cancer patients, cardiac catheterization for patients with compromised cardiovascular systems, and minimally invasive surgery procedures).

BACKGROUND

Newborns that need special care are placed in a specialized area, such as a neonatal intensive care unit (NICU) within a hospital. Pre-, post and term sick newborns that require a special environment are kept in an incubator (at temperatures up to 39 deg C., humidity up to 100% and oxygen up to 100%), and can be coupled to several life sustaining devices (e.g., a ventilator for artificial breathing, transfusion pumps for delivering the exact amount of fluids necessary for survival of the newborn, intra-venous (I/V) bags for delivering saline or glucose, etc.). Additionally, vital signs monitoring equipment (e.g., electrocardiogram (ECG), electroencephalogram (EEG), blood saturation oxygen levels, carbon dioxide build up levels, blood pressure, body temperature, etc.), which generally have several lines (e.g., monitoring lines for ECG, EEG, $O_2$, $CO_2$, temperature and pressure), are coupled to the newborn at all times for continuous care and monitoring.

Severely ill newborns that demand special care generally are left in the NICU and are not transported to other hospital sections for diagnostic procedures, such as X-ray, computer tomography (CT), magnetic resonance (MR), etc. Additionally, clinical interventions, such as radiation therapy for cancer patients, cardiac catheterization for patients with compromised cardiovascular systems, and minimally invasive surgery procedures in or near the diagnostic scanners also are generally not performed on severely ill newborns. Thus, diagnosis and treatment is limited to moderately ill newborns and generally is not extended to severely ill newborns. This is unfortunate.

Magnetic resonance is a premier diagnostic tool and is used routinely in the characterization of illness in the first few hours of life. Newborns with illness of the brain, heart or major organs in the torso and pelvis (e.g., liver, kidney, spleen, etc.) are often transported in a regular non-MR compatible transport incubator to the MR system. Prior to being scanned in the MR system, the life sustaining and monitoring lines of the transport incubator are uncoupled from the newborn, and a local set of lines are re-coupled to the newborn. The patient then is removed from the transport incubator and placed on a magnetic resonance imaging (MRI) table. Subsequently, the patient is imaged in a super cooled MR scanner using adult sized radio-frequency (RF) coils. Once the imaging procedure is completed, the patient is placed back in the transport incubator, the local lines are uncoupled, the transport incubator lines are re-coupled, and the patient is transported back to the NICU in the transport incubator. Clearly, the newborn's environment is disturbed on multiple occasions prior to, during and after an MR scan.

Moreover, because of the disturbance to the newborn's environment, patients with compromised thermoregulatory systems are rarely scanned due to their need for a highly controlled environment. This necessitates that a controlled environment (e.g., an incubator) be provided along with all the life sustaining and vital signs monitoring equipment during all stages of the MR scan, including transport to the MR system, the MR scan, and transport back to the NICU.

Diagnosis/prognosis using MR depends on MR image quality. Newborns placed in adult sized coils have a low filling factor, which results in low signal-to-noise ratios (SNRs). Given the smaller physical size of newborns, higher imaging resolutions are sought in smaller volumes, which further reduce the SNR. Custom RF coils are sought to address the loss in SNR and to reduce the stay of the newborn in the MR scanner.

Accordingly, an incubator used in MR scanning should not adversely affect the image quality produced from an MR scan. Moreover, to protect the patient's health and safety, the MR scanner must not adversely affect the operation of the incubator.

An incubator for tomographic examination was disclosed by Koch et al. (U.S. Pat. No. 5,800,335 issued Sep. 1, 1998), and is of a modular design. This incubator, however, fails to encompass a complete sub-system. For example, the incubator disclosed in Koch et al. requires additional components to transport an infant to/from the MR scanner and does not include life sustaining equipment or vital signs monitoring equipment. Additionally, while the incubator design is novel, the heater switching circuitry can produce artifacts during MR scanning and, therefore, degrade the image quality of the MR scan. Furthermore, during imaging the incubator is placed inside an RF coil, which results in a low filling factor, thus degrading the image quality.

The concept of an RF coil inside an incubator was introduced by Nordell et al. (see International Publication Number WO98/48756 A1, issued Nov. 5, 1998). More particularly, a receive only RF coil was introduced inside the incubator for effective scanning. Fluid flow turbines or related technology circulate the air inside the incubator to achieve even temperatures in the incubator volume. A stand-alone monitor in the base unit, which is situated near the MR patient table, monitors and displays the patient's vital signs. Vital signs monitoring lines typically span from the MR patient table, where the patient is placed, to the base unit at the foot of the MR patient table inside the MR room. The unit worked as proposed, but the long line spans hampered efficient performance as they obstructed patient care. For example, when immediate access to the patient was sought, one had to juggle his/her way through the maze of lines.

A novel solution to this problem was addressed by Rohling et al. (U.S. Pat. No. 6,611,702 issued Aug. 26, 2003) wherein the entire incubator and monitoring unit are built on a General Electric (GE) MR patient table. The unit, however, is bulky and difficult to maneuver, particularly in a hospital environment. Generally, a minimum of three people are required to maneuver the unit from the NICU to the MR section. Additionally, the incubator is not modular and the entire unit must be transported together, which limits access to certain sections of the hospital.

Recently an application for patent for an MR compatible incubator/transporter system was filed by Lonneker-Lammers (see EP20010109195 20010412, filed April 2002 and WO 02-083053A1, filed Apr. 12, 2002). With this MR compatible incubator system, safe transport is possible between the NICU and the MR sections, and the patient is left undisturbed from the time he/she is transported from the NICU to the MR scanner, during the MR scan, and transported back to the NICU. Improvements to the RF coil design for high SNR were made by Srinivasan (U.S. Application Ser. No. 60/722, 760 filed Nov. 26, 2003).

The above described systems, however, do not provide a complete solution for newborn care, transport and MR scanning. Accordingly, there is a need in the art for a self-contained neonate imaging sub-system, including an MR compatible incubator, MR compatible life sustaining and monitoring equipments, MR compatible ventilator, MR compatible infusion pumps, MR compatible injectors, and high SNR RF coils, all of which can be used to care for, to transport, to perform clinical interventions and to image the patient without significantly disturbing the microenvironment of the incubator.

SUMMARY OF THE INVENTION

An aspect of the invention relates to a radiology imaging sub-system for treating neonates, including: a radiology compatible incubator for providing a controlled environment for a neonate; a radiology compatible RF coil selectively coupled to the incubator for providing radiological imaging of the neonate; and a radiology compatible trolley for transporting the incubator and the RF coil.

To the accomplishment of the foregoing and related ends, the invention, then, comprises the features hereinafter fully described and particularly pointed out in the claims. The following description and the annexed drawings set forth in detail certain illustrative embodiments of the invention. These embodiments are indicative, however, of but a few of the various ways in which the principles of the invention may be employed. Other objects, advantages and novel features of the invention will become apparent from the following detailed description of the invention when considered in conjunction with the drawings.

BRIEF DESCRIPTION OF DRAWINGS

These and further features of the present invention will be apparent with reference to the following description and drawings, wherein:

FIG. 3A is an isometric view of an incubator and a movable patient table for re-intubation in accordance with an embodiment of the present invention, wherein the patient table is positioned inside the incubator;

FIG. 5B is an isometric view of a Neonate Integrated Head Spine Array, suitable for imaging the brain, neck, shoulders, and entire spine of infants.

DISCLOSURE OF INVENTION

Figure 1:
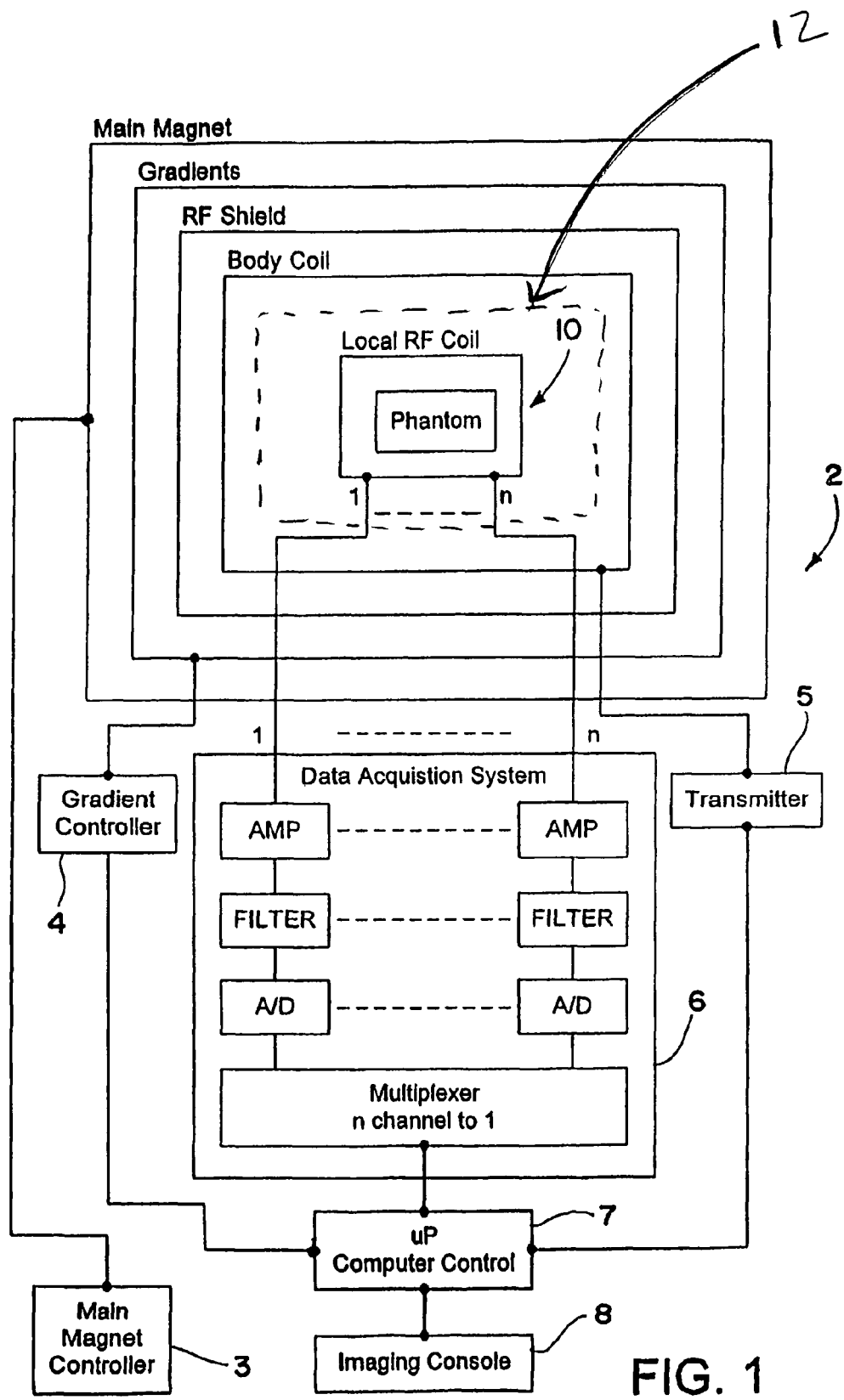
FIG. 1 is a block diagram of a magnetic resonance system that can be used in conjunction with the neonate imaging sub-system of the present invention.

The following is a detailed description of the present invention with reference to the attached drawings, wherein like reference numerals will refer to like elements throughout.

The neonate imaging sub-system of the present invention will be described with respect to a magnetic resonance imaging system. It should be appreciated, however, that the present invention can be used in other radiology systems, including computer tomography imaging, x-ray imaging, fluoroscopic imaging, etc., without departing from the scope of the invention. For example, a neonate imaging sub-system that is compatible with magnetic resonance imaging systems, also is compatible with computer tomography imaging systems, flouroscopic imaging systems and x-ray imaging systems (provided the target area to be imaged is not shielded by a metallic component).

Referring to FIG. 1, a block diagram of an MR system 2 that can be used in conjunction with a neonate imaging sub-system in accordance with the present invention is shown. The MR system 2 includes a main magnet controller 3, a gradient controller 4, a transmitter 5 and a data acquisition system 6, as is conventional. A computer controller 7 controls the operation of the system, and system data is provided to a user through an imaging console 8. A coil 10 of the neonate imaging sub-system 12 sends and receives data to/from the data acquisition system 6.

Figure 2:
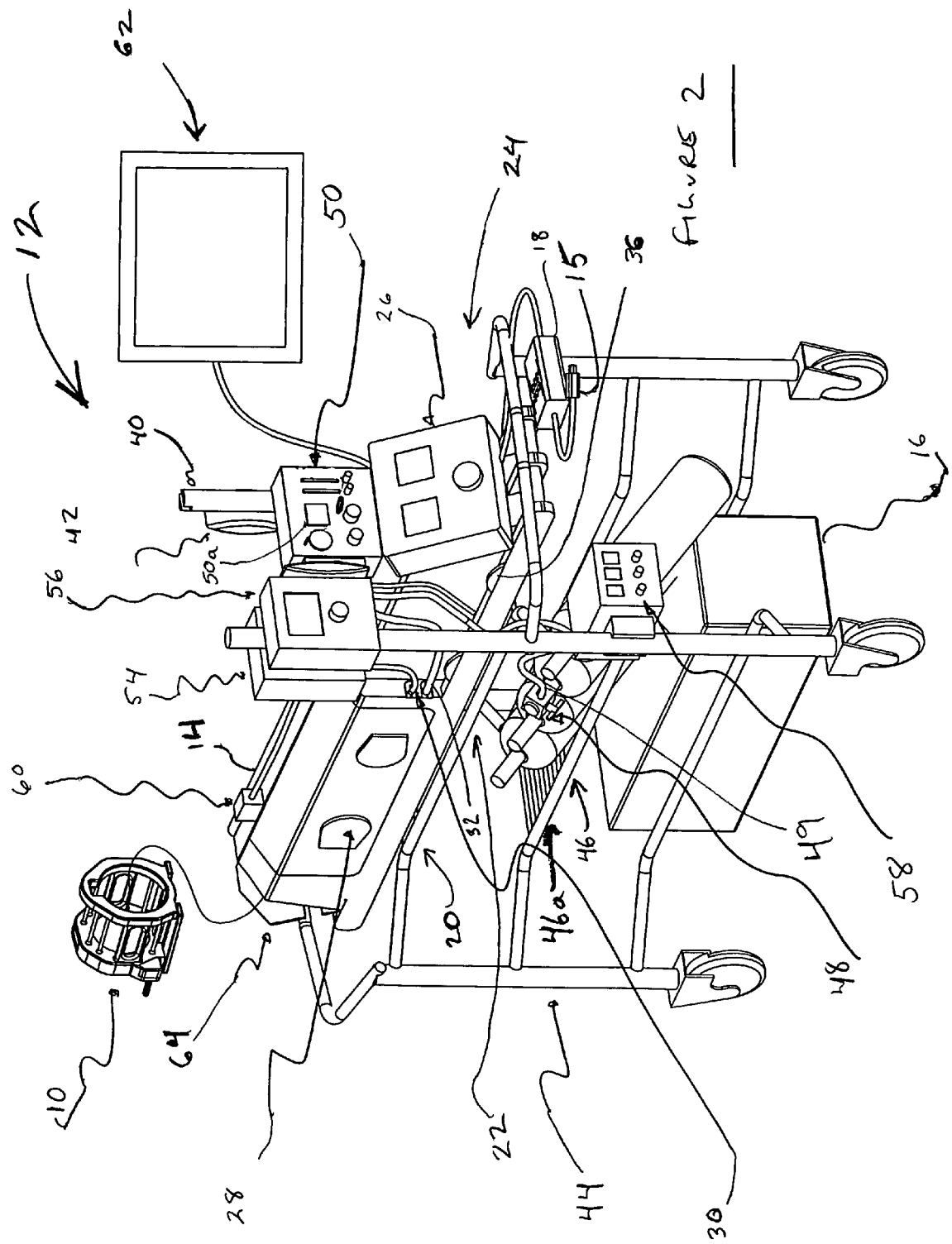
FIG. 2 is an isometric view of a neonate imaging sub-system in accordance with an embodiment of the present invention.

Referring now to FIG. 2, an MR compatible neonate imaging sub-system 12 in accordance with an embodiment of the present invention is shown. The sub-system 12 includes various components, such as life sustaining equipment, vital signs monitoring equipment, and controlled environment equipment. Additionally, the neonate imaging sub-system can be modular, which facilitates removal and/or installation of various sub-components. For example, additional or different vital sings monitoring equipment easily can be added to and/or removed from the sub-system via quick release couplings. As used herein, a modular component is a component that quickly and easily can be added to and removed from the sub-system 12. Generally, such modular components are coupled to the sub-system using hand operable locking clasps, for example. It is contemplated, however, that in some instances it may be preferable to use a relatively more secure coupling means, such as a screw type fasteners or the like, to couple a component to the sub-system. Furthermore, the modularity of the sub-system facilitates transporting the sub-system to various locations. If a component is not required, it easily can be removed, thus reducing the weight and size of the sub-system.

The entire sub-system 12 is MR compatible, which permits safe and effective radiographic examination of the subject without affecting the incubator performance or the image quality. Moreover, the newborn can remain in the incubator during the transport to and from the MR scan room as well as during the MR scan. This facilitates the well-being of the newborn, as his/her micro environment is not disturbed. Additionally, life sustaining and monitoring lines can remain coupled to the infant at all times, even during MR scanning. The components of the neonate imaging sub-system will now be discussed in more detail.

Throughout this disclosure reference will be made to MR compatible components, e.g., an MR compatible monitor or an MR compatible ventilator. Details on fabricating and/or modifying such components for compatibility with MR are provided in U.S. Patent Application Ser. No. 60/723,325 filed Nov. 26, 2003 and titled IMPROVED COMPATIBILITY OF ACCESSORY OF MAGNETIC RESONANCE, which has been incorporated by reference. Accordingly, details regarding how to prepare a component or components for MR compatibility will not be discussed in detail herein.

Briefly, interference with static magnetic fields can be reduced or eliminated by using non-interference generating components, such as non-magnetic components and/or non-conductive, non-metallic plastic components. These types of components do not produce a water signal, have very little or no leakage electrical currents (below 10 milliamps), and very little or no eddy currents. Thus, artifacts due to the components can be reduced and/or eliminated. For example, circulating currents within the components that can come in contact with the subject can be eliminated through the use of non-conductive materials, which are intended to enhance patient safety.

Additionally, the components should be transparent to the main magnetic field of the MR system 2. Metal components should be non-magnetic (e.g., strontium, phosphor-bronze, beryllium-copper, copper, aluminum, silver, gold etc.) and preferably have a low permeability, e.g., a permeability that will cause less than 1 percent eddy currents, ghosting and/or distortion of the image in all three axis X, Y, Z, respectively, particularly in low signal to noise scans with echo times less than 2.0 milliseconds. In most cases, diamagnetic and ferro-magnetic materials should be limited, and in some cases diamagnetic and ferro-magnetic materials should not be used.

Interference due to time varying gradient magnetic fields can be reduced using intermediate frequency (IF) filters. For example, IF filters and feed-thru capacitors can be placed in all signal lines (e.g., data carrying lines), wherein the feed-thru capacitors either block all of the interferences or shunt them to ground. Additionally, gradient interferences can be minimized by reducing the size of the metals used in shielding the incubator electronics or by keeping them away from the gradient field of view (FOV). Ghosting or aliasing can be minimized by eliminating moving metal parts and by placing the metal sections away from the gradient cross-overs along the magnet axis.

RF interference can be minimized by appropriate filtering mechanisms in passive signal lines and the active lines (lines that carry power). RF chokes can be used to prevent RF leakage, whereas high power RF filters capable of carrying a few amperes with very high impedances can be utilized.

Incubator

The neonate imaging sub-system 12 includes an incubator 14, which can be a portable, modular unit (e.g., it may be detached and removed from the sub-system 12). In one embodiment, the incubator can be removed from the trolley and placed on the radiographic or radiotherapy patient table, so diagnosis and/or treatment procedures can be performed. The incubator 14 includes two handles, e.g., front and rear (not shown) and is designed to be lifted by two people on to an MR patient table. The width, length and height of the incubator 14 are chosen to permit easy transport through narrow hallways, elevators, and rooms of a hospital, as well as for compatibility with most MR, CT and X-ray patient tables. For example, the unit can weigh approximately 45 kilograms, can be about 16 inches tall and 7 feet long and 15 inches wide. The incubator can be coupled to an AC power source, e.g., a 115 VAC outlet, via a power connector 15, or it can be driven by an onboard battery 16. A power supply 18, which includes an isolation transformer for patient safety, converts the battery power or the external AC supply to the proper voltage levels required by the system 12. The isolation transformer should be located remote from the incubator (e.g., six feet from the incubator) in order to prevent interference during an MR scan. If it is not feasible to locate electro-magnetic components (e.g., transformers, electric motors, etc.) remote from the incubator, then the electromagnetic components should be shielded (e.g., placing a metal shield around an electric motor, shielding wires routed to/from the motor, etc.)

The incubator 14 includes three sections, the first of which is a double walled (to minimize heat transfer due to convection or radiation) patient section 20. The patient section is transparent and, thus, permits complete visual contact of the patient at all times. This section is radio-translucent, which permits CT, x-ray and fluoroscopic imaging techniques and radiation studies to be performed without artifacts. The plastic used in this section does not provide a water signal, which can cause imaging artifacts and interfere with the image diagnosis. The second section is the aggregate section 22, which houses sensors (e.g., temperature, humidity, and oxygen), heater and humidity generators, and a blower, which is required for forced air circulation. The third section is the electronics section 24, which includes feedback/control/monitoring circuits for maintaining the prescribed temperature, humidity and oxygen concentration inside the patient compartment. Additionally, the electronics section 24 can include an operator interface 26 with visual/audible alarms, etc.

Temperature feedback can be based either on the air temperature measured in the patient section 20 or the skin temperature continually monitored at the axilla (under the arm) or the belly of the patient. Humidity can be generated by hygienically boiling water. For example, fresh air can be drawn in from the ambient environment surrounding the incubator 14 through a particle filter (not shown), warmed and humidified inside the aggregate section 22, and then supplied to the patient section 20. The air circulating through the patient section 20 can be forced back through a narrow nozzle, and a small fraction of this air can be re-circulated to the patient section.

Since only a small amount of air is recirculated, carbon dioxide ($CO_2$) build up inside the patient section 20 is not significantly increased. $CO_2$ build up inside the incubator less than 0.5% is deemed safe for use with ill newborns.

The patient section 20 of the incubator 14 includes double-walled hand ports 28 that facilitate easy access to the patient. Portals 30 can be provided at either end of the incubator 14, for example, for allowing life sustaining/monitoring lines 32 to be coupled to the patient. Additionally, the portals can be used for RF coil connections, which can traverse from an RF coil 10 (which is in the patient section) to the MR scanner. Small semi-circular flaps 36 outside the aggregate section and alongside the incubator 14 are designed to hold the lines extending out from the patient section and connecting to the respective devices. Thus, the flaps hold the lines during transport and, therefore, minimize the possibility of the lines becoming pinched during transport or movement of the incubator (e.g., moving the incubator on and/or off the trolley and the MR patient table). As will be appreciate, other holding means may be employed, such as clamps, fasteners, or the like.

Figure 3B:
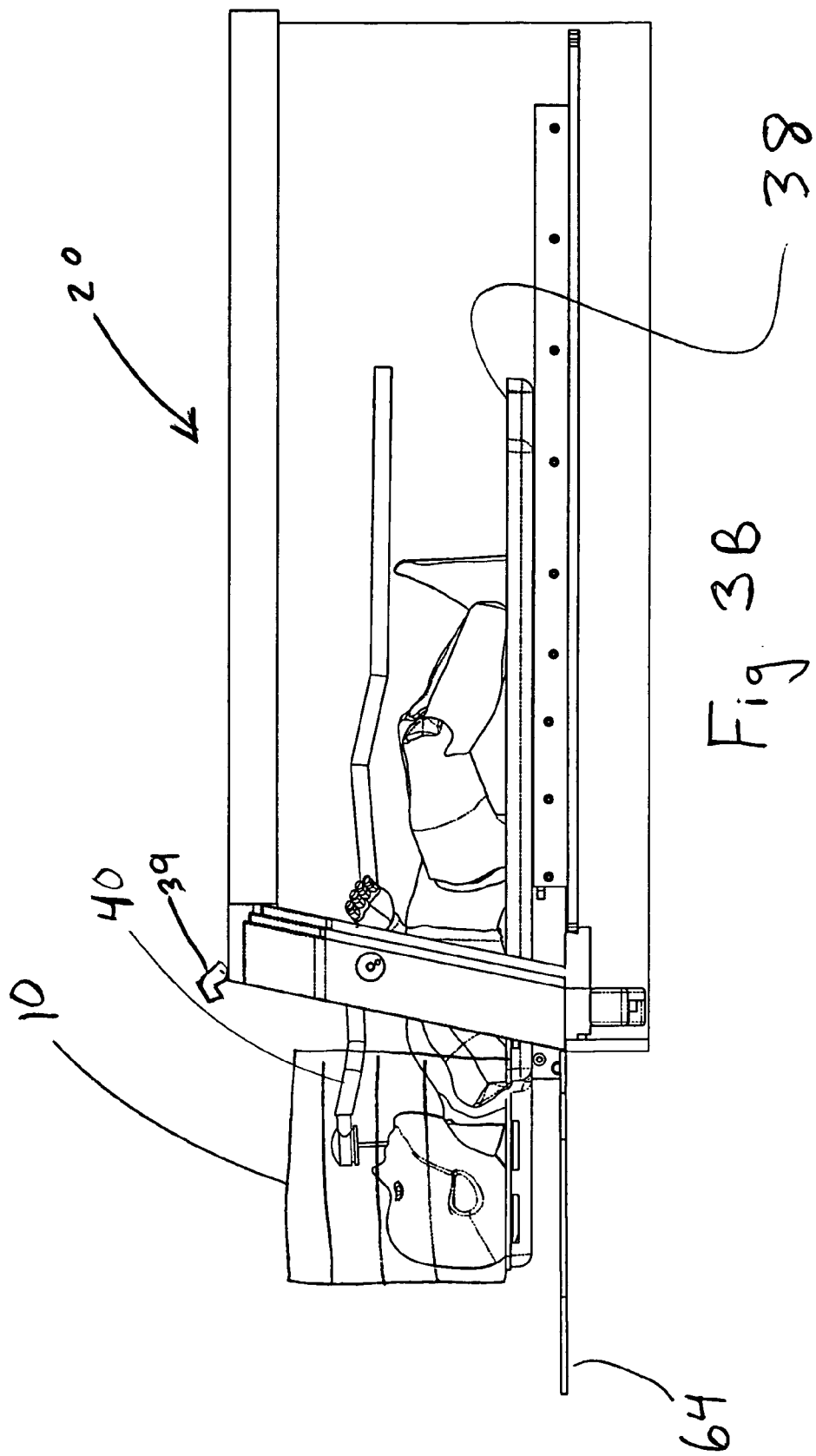
FIG. 3B is an isometric view of an incubator and a moveable patient table for re-intubation in accordance with an embodiment of the present invention, wherein the patient table is positioned outside the incubator.

With further reference to FIGS. 3A and 3B, the patient section 20 includes a small patient table 38 to accommodate the tiny newborn patient. A quick latch mechanism 39 can be included that allows the patient table 38 to slide past the incubator 14 in a longitudinal fashion (e.g., along the incubator long axis) to allow immediate access to the patient. As will be appreciated, the type of mechanism 39 and its location with respect to the patient table 38 can vary based on the specific design implemented for the quick latch mechanism.

The quick latch mechanism is advantageous, especially in a transport system. For example, should the patient go into shock, stop breathing, have a stroke, etc, immediate access to the patient is available, thereby facilitating resuscitation efforts. While resuscitation efforts are carried out, it is further advantageous that the life sustaining or monitoring lines be coupled to the patient at all times, thereby permitting the status of the patient to be monitored. The moving table feature shown allows all (e.g., life-sustaining and monitoring) lines to remain connected to the patient with the incubator ON at all times prior, during and after resuscitation. It is noted that with the rear flap of the incubator open, the temperature of the incubator can drop by about 1-2 degrees, but the patient will still remain relatively warm.

As the patient table 38 is moved in/out of the incubator, the patient and the lines coupled to the patient will move with the patient table 38 and, therefore, not inhibit motion of the patient table 38. Also shown in FIGS. 3A and 3B is the placement of the coil 10 within the patient section 20. The coil 10 can move in and out of the patient section 20 with the patient table 38, or independently of the patient table, e.g., removing the coil from the patient section 20 of the incubator.

The incubator can include an IN pole 40 that has multiple functions. First, the pole 40 can support one or more I/V bags 42. Second, and as will be discussed below with respect to FIG. 4, the I/V pole can prevent the electronics section 24 of the incubator 14 from being placed within a magnet bore of the MR scanner, e.g., a mechanical stop. Alternatively, an electrical stop (not shown) can be used to disable the MR scanner if the incubator electronics section is placed in the magnet bore.

Electrical components within the incubator 14 are shielded to minimize interference with static magnetic fields. For example, a magnetic fan motor is shielded with a steel cylinder. The steel cylinder can have a thickness of about 1/16 inch, for example. Additionally, fasteners, such as steel screws and shafts (not shown), are replaced with beryllium-copper, phosphorous-bronze or aluminum, for example.

MR Compatible Trolley

An MR compatible trolley 44 is made of MR compatible material, such as non-conductive/non-metallic material, e.g., plastics and/or non-magnetic material, e.g., strontium, phosphor-bronze, beryllium-copper, copper, aluminum, silver, gold, etc. The trolley can include shock absorbers atop the unit where the incubator is placed, and shock absorbing struts couple each post to a corresponding rubber wheel. Locks are provided (not shown) on the wheels to restrict trolley motion, for example, during incubator transfer from the MR patient table to the trolley or during an emergency procedure performed outside of a routine area (e.g., in hallways, elevators, etc.) or during transport (e.g., in an elevator or a vehicle). The trolley can be contoured to fit in hallways and elevator doors typically found in hospitals (e.g., elevators 3 feet wide, 7 feet deep, and 8 feet tall). The trolley houses oxygen/air tanks, monitoring equipment, infusion pumps, injectors and the like with an easy connect/disconnect coupling mechanism (e.g., hand operable locking clasps or the like). All four wheels of the trolley can move independent of one another for easy maneuvering, e.g., independent rotation and/or dampening. The trolley is designed to provide a shock-free ride for the patient inside the incubator 14 while being robust enough for routine use in a hospital environment (sharp 90 degree bends, wheel chair accessible inclining/declining ramps, etc.). The components on the trolley can be turned OFF and kept inside the scan/therapy room or moved outside, for example, for re-charging the battery while the examination is carried out.

MR Compatible Oxygen/Air Tanks

Tanks 46, pressure reducers 48 and flow pipes 49 are fabricated from MR compatible material (e.g., aluminum, virgin brass without iron, phosphor-bronze, silver, etc.). The oxygen/air tanks 46 provide oxygen/air supply to the incubator 14 or directly to the patient via a nasal canula. Alternatively, for extremely sick patients, oxygen/air can be provided through a ventilator (discussed below). Pressure reducers 48 can be used to reduce the source pressure to the required oxygen concentration and flow rate prescribed by the physician. For example, the flow to the ventilator can be roughly 15 to 30 liters per minute (lpm), whereas flow to the nasal canula for the infant can be up to 3 liters per minute. The exact flow rate depends on the oxygen concentration provided to the patient.

The trolley 44, for example, can accommodate up to four tanks 46; two for oxygen and two for air. The tanks 46 can be coupled to a rack or tray 46a of the trolley 44. The pressure reducer 48 can be attached to one or more tanks 46 of a common type (e.g., one or more oxygen tanks, one or more air tanks), and a means can be provided (not shown) to turn the flow ON or OFF from each tank or both tanks. Separate flow pipes can be employed to measure the flow rates in the different ranges (0-3 lpm, 3-20 lpm, 10-50 lpm etc). As was noted previously, metallic MR safe components can be used to fabricate the tanks, or non-conductive non-metallic components such as fiberglass cylinders that can withstand high pressures (of up to 3000 psi) also can be used to fabricate the tanks. Conductive non-metallic cylinders made of carbon fiber, etc., are not recommended for use, since leakage currents greater than 10 mA can conduct through such tanks, which is above the leakage current safety standard for medical devices.

MR Compatible Ventilator

An MR compatible ventilator 50 with a built-in blender can be used with the incubator 14. The ventilator 50 is fabricated using MR compatible materials, such as, aluminum, pure brass, phosphor-bronze, etc. The unit can be placed atop the incubator 14 or over the electronics section 24. A ventilator display 50a is configured to face the operator at all times. Ventilators are used with patients who have a compromised respiratory system and thus are unable to breathe on their own. A blender (not shown) can be used in conjunction with the ventilator 50 to provide a precise mixture of oxygen/air concentration prescribed by the physician. The blender input is coupled to the oxygen/air tanks and the blender output is coupled to the ventilator. The inspiration/expiration rates, etc., that vary from patient to patient are set by controls on the ventilator 50. The flow rate is controlled by the ventilator and monitored from time to time by the NICU nurse or respiratory physician or technician. The ventilator is driven pneumatically and hence does not interfere with the performance of the incubator or the MR system.

A backup system is provided should the ventilator fail. The user can connect a mechanical aspirator (e.g., for positive pressure ventilation with a resuscitation bag or manual resuscitator, such as a balloon pumped by the human hand) to an auxiliary output of the blender to support the patient's breathing. Alternatively, the user can couple the oxygen/air lines directly to the ventilator 50 or to the patient. In either case, appropriate flow rates are maintained and controlled by the pressure reducers 48, flow tubes 49 and the ventilator 50 to prevent excess flow to the patient. This is important, for example, in patients with encephalopathy in the first few weeks of life. Should an over-abundance of oxygen be passed to such patients, damage to the eyes (hyperoxia) can result, or if insufficient oxygen is passed to the patient, damage to the brain (hypoxia) can result. Hence, the condition hypoxic-ischemic encephalopathy (HIE), or severe HIE in some cases can lead to cerebral palsy (CP). To monitor the breathing of the patient, sensor free breathing circuits that are MR safe should be used. These circuits minimize the chance of arcs, imaging artifacts due to the MRI gradients, and RF signals picked up by the circuits during imaging. In addition, appropriate length breathing circuits should be used, as shorter breathing circuits may disrupt the flow of air to the patient when the re-intubation table is pulled out. Likewise, longer circuits can remain tangled and can become caught under the patient table or under the incubator and thus disrupt patient air flow.

Since the ventilator remains atop the incubator, which is placed on the radiographic patient table, equipment malfunction cannot be monitored if the hospital personnel are outside the exam room. A remote monitor, such as a hand held remote monitoring device (not shown), can be coupled to the system. The remote monitor can provide information related to ventilator performance, such as alarm conditions, e.g., disconnected or tangled lines, patient information, e.g., breathing rates, or any other unusual activity related to the system, to the hospital personnel.

MR Compatible Infusion Pumps

MR compatible infusion pumps 54 are used to pass the appropriate amounts of sedation drugs and/or other drugs/fluids/serums to the patient as prescribed by the physician. The pumps must function properly (i.e., operate within design specifications) when in close proximity to the MR magnet, the MR system and the incubator. One or more pumps are attached to the trolley as shown in FIG. 2. Pumps normally are motor driven and motors generally are magnetic, unless non-magnetic versions, such as piezo motors, are used. All criteria used to make the incubator and trolley MRI compatible also must be exercised with respect to the motors. Further, the performance of the pump, the radiographic procedures, and the treatment procedures must not be affected by the motors. Since low dosage and low volumes are used for the tiny patient, the motor is generally running at very low speeds, which reduces the interactions with the exam. Nevertheless, all of the measures to maintain compatibility of medical devices must be exercised. It is safe to keep the injector motor roughly 6-8 feet from a self-shielded 1.5T MRI magnet.

MR Compatible Intravenous I/V Bags

Figure 4:
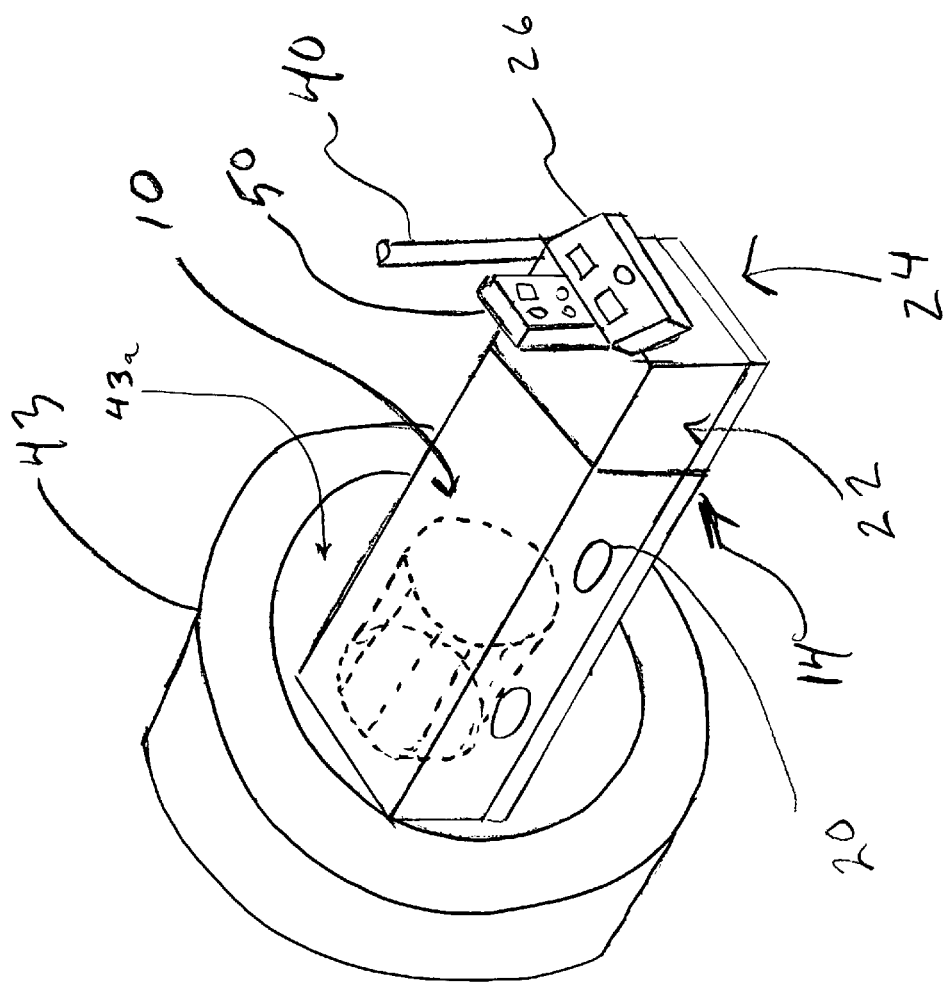
FIG. 4 is an isometric view showing the placement of the incubator in a magnet bore of a magnetic resonance scanning system.

As was noted previously, an MR compatible I/V pole 40 is coupled to the incubator 14. The MR compatible I/V pole 40 is made of non-conductive/non-metallic material, e.g., plastic and/or of non-magnetic materials, e.g., strontium, phosphor-bronze, beryllium-copper, copper, aluminum, silver, gold etc. Non-magnetic I/V poles made of aluminum are safe for use and well tested with MRI and other radiographic procedures. The I/V pole 40 allows one or more I/V bags 42 with MR compatible clips to be held atop the incubator 14 in close proximity to the MR magnet 43, as shown in FIG. 4. I/V fluids such as saline, glucose, etc., can be dispensed from the I/V bags 42. Additionally, and as was discussed previously, the I/V pole prevents the electronic section 24 of the sub-system 12 from being inserted into the magnet bore 43a of the MR scanner.

MR Compatible Injectors

MR compatible injectors 56 are used for careful administration of imaging contrast dyes to the patient during or between MR scans. Contrast studies assist to differentiate the tissues and their capability to perfuse/diffuse the medium. Diffusion weighted and perfusion weighted scans are run during this process for effective diagnosis/prognosis of the brain, its function, physiological status, etc. Pumps normally are motor driven and motors generally are magnetic, unless non-magnetic versions, such as piezo motors, are used. All criteria used to make the incubator and trolley MRI compatible also must be exercised with respect to the motors. Further, the performance of the pump, the radiographic procedures, and the treatment procedures must not be affected by the motors. Since low dosage and low volumes are used for the tiny patient, the motor is generally running at very low speeds, which reduces the interactions with the exam. Nevertheless, all of the measures to maintain compatibility of medical devices must be exercised. It is safe to keep the injector motor roughly 6-8 feet from a self-shielded 1.5T MRI magnet.

MR Compatible Monitor

Vital signs monitoring is important for infants with compromised thermoregulatory systems. Vital signs such as ECG, which measures heart rate and shape, Oxygen Saturation ($SpO_2$), which measures the patient's oxygen saturation in the blood, and Non-invasive Blood Pressure (NIBP), which measures blood pressure non-invasively, are used to determine the status of the patient. For example, NIBP is used to measure the patient's ejection fraction of blood pumping from the heart. Other vital signs monitoring include n tidal $CO_2$, which measures $CO_2$ build up (an increase in $CO_2$ should be a cause for alarm, high levels of $CO_2$ are deleterious to the health of the subject), and skin temperature, which serves to monitor the overall status of the patient and his/her ability to fight infections, etc. A monitor 58 can be coupled to the incubator 14 or attached to the trolley 44 as shown in FIG. 2. The feedback from each vital sign is displayed on the monitor. The monitor 58 must be MR compatible and must not produce artifacts during the MR scan. Preferably, a liquid crystal display (LCD) is used for the monitor. Alternatively, a cathode ray tube (CRT) display can be used as the monitor provided the monitor is properly shielded. For example, the CRT monitor should be shielded using an RF tight box. Regardless of the monitor type, all lines to/from the monitor should be routed with 100% shielded cables. The monitor must be tested for compatibility with the static main magnet MRI field, fast switching gradient fields in the intermediate frequency range and radio-frequency range for water protons (1H) and other nuclei (31P, 19F, 13C, 23Na etc.) used to image. Again, the performance of the monitor must be unaffected by the presence of the MRI and vice versa. The monitor should be kept a safe distance from the MRI equipment, e.g., generally 6-8 feet from a self-shielded 1.5T MRI magnet.

MR Compatible Fiber Optic Camera w/Remote Display

An MR compatible fiber optic camera 60 and remote display 62 can be used to monitor the patient at all times, especially when the subject is inside the magnet bore of the MR scanner. A remote display 62 can be used inside or outside the MR scan room for remote monitoring. Again, care must be ensured that the camera (preferably charge coupled device CCD or fiber-optic) and the display (preferably LCD) do not interfere with the performance of the incubator or the scanner.

Custom RF Coil

Details of a custom RF coil can be found in U.S. Application Ser. No. 60/722,760 titled IMPROVED RADIO FREQUENCY COIL FOR RESONANCE IMAGING ANALYSIS OF PEDIATRIC PATIENTS, the contents of which has been incorporated by reference. The custom head RF coil fits the 95th percentile of the newborn population up to 3 months of age. It is envisaged that after 3 months infants generally do not require an incubator. Anterior access to the patient is provided in the coil design, which also helps in the visual monitoring of the infant. The coil 10 is selectively couplable to the incubator and, therefore, can be quickly and easily inserted/removed from the incubator 14, e.g., by opening the rear flap 64 through which it the coil is introduced. The coil 10 can be held in place by groove rails, e.g., by sliding a portion of the coil under the grooved rails provided (not shown) inside the patient section 20 of the incubator 14. The coil design incorporates the possibility of the coil being exposed to a relatively high temperature (up to 39 deg C.), high levels of humidity (of up to 100% rH) and high levels of oxygen (up to 100%). Thus, the coil is designed to withstand the harsh incubator environment without compromising the safety of the experiment and the SNR. All of the electronics inside the coil are sealed with suitable fiberglass and/or epoxy resins to prevent interaction with the harsh environment typically found inside the incubator 12.

Neonate Body Coil

Figure 5A:
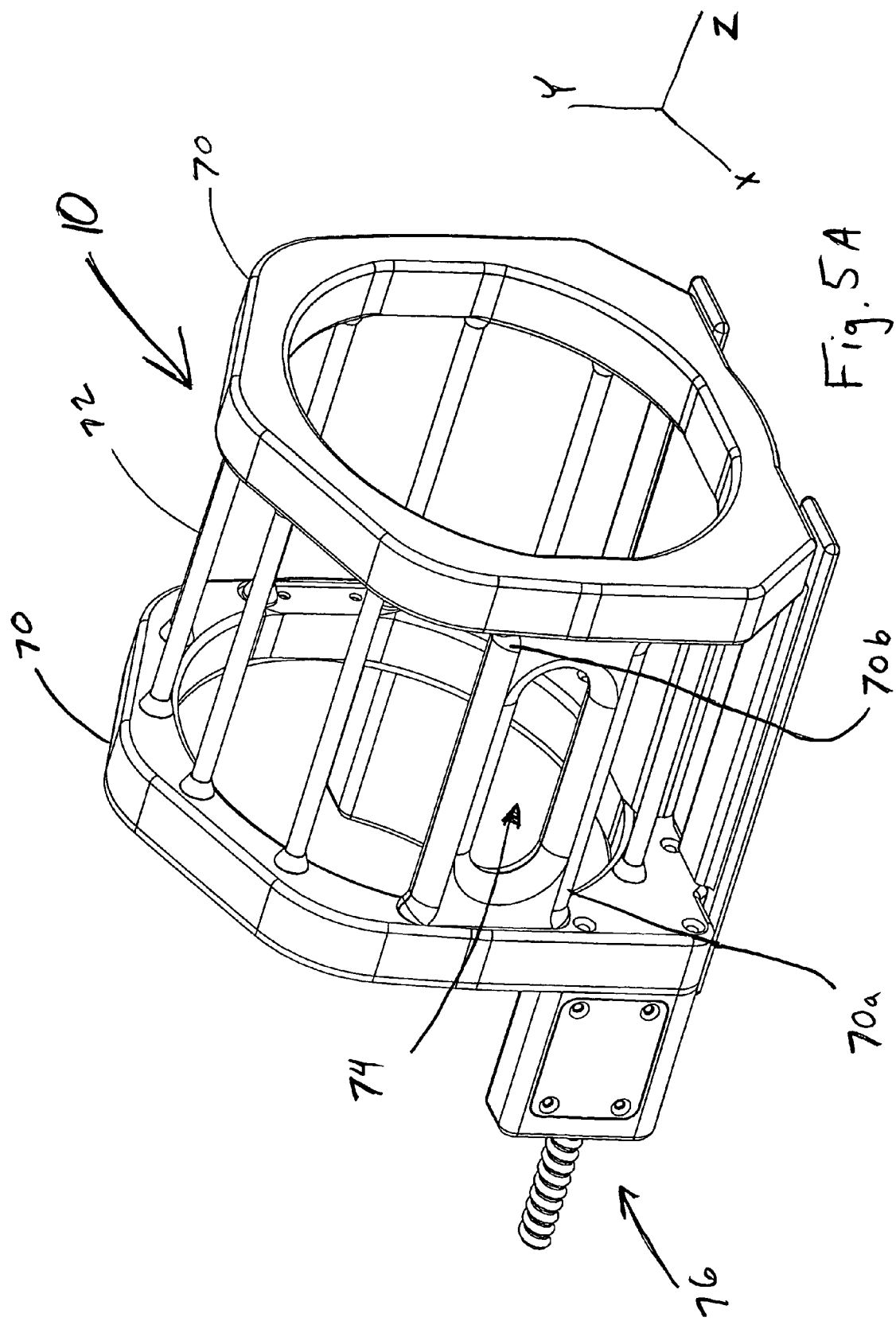
FIG. 5A is an isometric view of a neonate body coil for imaging neonate torsos and extremities, e.g., heart, lungs, abdomen, pelvis, arms, legs, etc.

With reference to FIG. 5A, an embodiment of an elliptical coil 10 that can be used in the transport system 12 is illustrated. The coil 10 is ergonomically designed to fit infants weighing up to 4.5 Kg and $95^{th}$ percentile of the newborn population. Coil dimensions, for example, can be 8.5 inches wide, 7.5 inches tall, 7.5 inches long, and suited for a sagittal/coronal Field-of-view (FOV) of 15-16 cm (along the length of the patient in the Z direction). The FOV is large enough to image the entire spine, heart, lungs or abdomen of the patient. Patients with heart conditions and/or congenital problems of the major organs can be safely transported and imaged using the system. Due in part to its smaller size, the coil 10 provides high signal to noise ratios (in comparison to adult sized coils routinely used to image infants) and, therefore, higher resolution imaging can be performed. Higher resolution imaging may facilitate precise diagnosis and in turn possibly early diagnosis, which can save precious lives.

The coil 10 has two end rings 70 connected by a plurality of straight segments 72 (legs). The end rings 70 of the coil 10 are shaped accordingly to accommodate an infant attached to life sustaining equipment (e.g., ventilator, anesthesia) and vital signs monitoring equipment (e.g., electrocardiogram, pulse oximeter, etc.). The two legs 70a, 70b toward a side of the coil 10 include an access way 74, which can be used to route life sustaining and/or monitoring lines to the patient. Electrical connections 76 provide a means to energize the coil 10 and receive imaging data from the coil 10, as is conventional.

Neonate Integrated Head-Spine Array

With reference to FIG. 5B an integrated head-spine array 80 that also can be used with the transport system 12 is shown. The integrated head-spine array includes a coil 10, as illustrated in FIG. 5A, and a table or platform 82 integrally formed with the coil. The integrated head-spine array facilitates diagnosis of neurological, anatomical and functional problems associated with the brain, spine and major organs (heart, liver etc). Sagittal/coronal imaging FOVs of 30 cm can be set to cover the entire brain and spine in one clinical exam.

The neonate imaging sub-system 12 of the present invention provides a complete solution for new born care. Newborns can be placed within the incubator 14 of the sub-system 12, thereby providing a controlled environment during the first few hours or weeks of their lives. Additionally, should MR scans be required, the newborn can be transported from the NICU to the MR scanner, scanned in the MR scanner, and transported back to the NICU, without being removed from the incubator or being decoupled from the life sustaining and monitoring equipment. Since the entire sub-system 12 is MR compatible, little or no interference is generated by the sub-system during the MR scan. Therefore, the sub-system 12 can remain near the MR scanner, or in the case of the incubator, in the MR scanner, during the MR scan, without affecting image quality.

Although particular embodiments of the invention have been described in detail, it is understood that the invention is not limited correspondingly in scope, but includes all changes, modifications and equivalents coming within the spirit and terms of the claims appended hereto.

What is claimed is:

1. A radiology imaging sub-system for treating neonates, comprising:
   a radiology compatible incubator for providing a controlled environment for a neonate;
   a radiology compatible RF coil selectively coupled to the incubator for providing radiology imaging of the neonate;
   at least one retaining mechanism coupled to the incubator for retaining at least one of a life sustaining line or a life monitoring line to the sub-system,
   wherein the retaining mechanism is a semicircular flap coupled to at least one of the incubator, the trolley or the coil; and
   a radiology compatible trolley for transporting the incubator and the RF coil,
   wherein the incubator and RF coil are formed as a modular assembly thereby facilitating installation and removal of the incubator and RF coil to/from the sub-system.

2. The sub-system of claim 1, further comprising at least one radiology compatible device selected from the group consisting of a radiology compatible vital signs monitor, a radiology compatible infusion pump, a radiology compatible injector, a radiology compatible ventilator, a radiology compatible blender, and a radiology compatible intravenous pole.

3. The sub-system of claim 2, further comprising:
   a radiology compatible camera coupled to the incubator; and
   a radiology compatible display, wherein images captured by the camera are viewable on the display.

4. The sub-system of claim 2, wherein at least one radiology compatible device is modular, thereby facilitating installation and removal of each component to/from the sub-system.

5. The sub-system of claim 2, wherein the blender is a pneumatic blender.

6. The sub-system of claim 1, further comprising:
   a radiology compatible camera operatively coupled to the incubator; and
   a radiology compatible display, wherein images captured by the camera are viewable on the display.

7. The sub-system of claim 6, wherein the camera is a fiber optic camera.

8. The sub-system of claim 6, wherein the display is remotely located relative to the camera.

9. The sub-system of claim 1, further comprising means for retaining at least one of a life sustaining line or a life monitoring line to the sub-system.

10. The sub-system of claim 1, further comprising a moveable patient table operatively coupled to the incubator, said movable patient table facilitating quick access to a patient in the incubator.

11. The sub-system of claim 10, wherein the moveable patient table is retained by a quick release latch.

12. The sub-system of claim 1, wherein the incubator, trolley and coil are fabricated from the group consisting of aluminum, virgin brass, phosphor-bronze, silver and plastic.

13. The sub-system of claim 1, wherein the sub-system receives power from an external source.

14. The sub-system of claim 1, wherein the subsystem receives power from an onboard source.

15. The sub-system of claim 14, wherein the onboard source is a battery pack.

16. The sub-system of claim 1, further comprising:
a radiology compatible vital signs monitor;
at least one radiology compatible oxygen/air tank;
at least one radiology compatible pressure reducer operatively coupled to the at least one oxygen/air tank; and
at least one radiology compatible intravenous pole.

17. The sub-system of claim 16, further comprising:
a radiology compatible ventilator;
at least one radiology compatible ventilator monitor;
at least one radiology compatible blender;
a radiology compatible infusion pump; and
a radiology compatible injector.

18. The sub-system of claim 1, wherein the radiology medium is at least one of magnetic resonance imaging, computer tomography imaging, flouroscopic imaging, and x-ray imaging.

19. The sub-system of claim 1, wherein the radiology compatible RF coil is an RF head coil, further comprising an RF body coil selectively coupled to the incubator for providing radiology imaging of a body of the neonate.

20. The sub-system of claim 1, wherein the radiology compatible RF coil comprises an integrated head-spine array for diagnosis of neurological, anatomical and functional problems associated with the brain, spine and major organs of the neonate.

21. The sub-system of claim 1, wherein the modular assembly includes hand-operable fasteners for facilitating removal and/or installation of the at least one incubator and RF coil to/from the sub-system.

22. A radiology imaging sub-system for treating neonates, comprising:
a radiology compatible incubator for providing a controlled environment for a neonate;
a radiology compatible RF coil selectively coupled to the incubator for providing radiology imaging of the neonate;
a flap through which the RF coil can be inserted into the incubator and removed from the incubator through the flap; and
a radiology compatible trolley for transporting the incubator and the RF coil,
wherein the incubator and RF coil are formed as a modular assembly thereby facilitating installation and removal of the incubator and RF coil to/from the sub-system.

* * * * *